United States Patent
M S et al.

(10) Patent No.: US 11,978,201 B2
(45) Date of Patent: May 7, 2024

(54) METHOD AND DEVICE FOR DETERMINING THE CONCENTRATION OF ANALYTES IN A SAMPLE

(71) Applicant: Siemens Healthcare Diagnostics Inc., Tarrytown, NY (US)

(72) Inventors: Ragavendar M S, Flanders, NJ (US); Mohiudeen Azhar, Bangalore (IN); Kalpesh Mehta, Singapore (SG)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 635 days.

(21) Appl. No.: 17/265,995

(22) PCT Filed: Jul. 31, 2019

(86) PCT No.: PCT/US2019/044375
§ 371 (c)(1),
(2) Date: Feb. 4, 2021

(87) PCT Pub. No.: WO2020/033203
PCT Pub. Date: Feb. 13, 2020

(65) Prior Publication Data
US 2021/0166386 A1 Jun. 3, 2021

Related U.S. Application Data

(60) Provisional application No. 62/716,441, filed on Aug. 9, 2018.

(51) Int. Cl.
G06T 7/00 (2017.01)
B01L 3/00 (2006.01)
G01N 33/49 (2006.01)

(52) U.S. Cl.
CPC .......... G06T 7/0012 (2013.01); B01L 3/5027 (2013.01); G01N 33/49 (2013.01); *G06T 2207/30101* (2013.01)

(58) Field of Classification Search
CPC ......... G06T 7/0012; G06T 2207/30101; B01L 3/5027; G01N 33/49; G01N 33/491; G01N 1/4077; G01N 21/31
See application file for complete search history.

(56) References Cited

U.S. PATENT DOCUMENTS 6,235,536 B1 * 5/2001 Wardlaw ............ G01N 33/5002
436/805
6,819,408 B1 11/2004 Scrivens et al.

FOREIGN PATENT DOCUMENTS

EP 2793015 A1 * 10/2014 ........... A61B 5/1455
EP 2793015 A1 10/2014

OTHER PUBLICATIONS

European Search Report and Written Opinion of European Application No. 19847086.6 dated Aug. 24, 2021.
(Continued)

*Primary Examiner* — Said M Elnoubi

(57) ABSTRACT

A method and a device for determining a concentration of one or more analytes in a whole blood sample is disclosed. In one aspect of the invention, the method includes introducing the sample in a channel. The method further includes generating a cell-free plasma region in the channel, wherein the cell-free plasma region is generated in the channel based on rouleaux effect. The method further includes illuminating the sample with light having varying wavelengths. Additionally, the method includes obtaining an image of the illuminated sample at each of the wavelengths. Furthermore, the method includes analyzing the image to determine the concentration of the one or more analytes.

14 Claims, 4 Drawing Sheets

(56) References Cited

OTHER PUBLICATIONS

Crowley et al., "Isolation of plasma from whole blood using planer microfilters from lab-on-a-chip applications", Jul. 19, 2005 (Jul. 19, 2005), Lab On A Chip; vol. 5, No. 9, pp. 922-929.
Durc et al, "Fast blood plasma separation device for point-of-care applications", Feb. 8, 2018 (Feb. 8, 2018), Talanta; vol. 183, pp. 55-60.
International Search Report and Written Opinion of International Application No. PCT/US2019/044375 dated Oct. 10, 2019.
Mauk et al., "Integrated Microfluidic Nucleic Acid Isolation, Isothermal Amplification, and Amplicon Quantification", Microassays, Oct. 20, 2015, vol. 4; pp. 474-489.
Davis et al., "Deterministic hydrodynamics: Taking blood apart", PNAS, Oct. 3, 2006, vol. 103, No. 40, pp. 14779-14784.
Maria et al., "Capillary flow of blood in a microchannel with differential wetting for blood plasma separation and on-chip glucose detection", Biomicrofluidics, Sep. 2016, 10(5), pp. 1-15.
Homsy et al., "Development and Validation of a Low Cost Blood Filtration Element Separating Plasma from Undiluted Whole Blood", Biomicrofluidics, Mar. 2012, 6(1), pp. 1-9.
Tripathi et al., "Microdevice for plasma separation from whole human blood using biophysical and geometrical effects", Scientific Reports 6, Article No. 26749, Jun. 2016, pp. 1-15.
Chen et al., "Microfluidic chip for plasma separation from undiluted human whole blood samples using low voltage contactless dielectrophoresis and capillary force", Lab Chip, 2014, vol. 14, No. 12, pp. 1-7.
Haeberle et al., "Centrifugal extraction of plasma from whole blood on a rotating disk", Lab Chip, 2006, 6, pp. 776-781.
Lenshof et al., "Acoustic whole blood plasmapheresis chip for prostate specific antigen microarray diagnostics", Analytical Chemisty, Aug. 1, 2009, vol. 81, No. 15, pp. 6030-6037.

* cited by examiner

METHOD AND DEVICE FOR DETERMINING THE CONCENTRATION OF ANALYTES IN A SAMPLE

The subject application claims benefit under 35 USC § 119(e) of U.S. provisional Application No. 62/716,441, filed Aug. 9, 2018. The entire contents of the above-referenced patent application are hereby expressly incorporated herein by reference.

FIELD OF TECHNOLOGY

The present disclosure relates to the field of analysis of a sample and more particularly to the field of determining the concentration of analytes in the sample.

BACKGROUND

Hemolysis is a phenomenon wherein the blood cells rupture in whole blood, releasing their content into the blood plasma. This condition may occur due to various reasons such as immune reactions, infections, and medications. Hemolysis may occur within the body of an individual or after the blood has been extracted out of the body. A major cause of hemolysis is the pre-analytical steps of blood sample handling, including collection of the blood sample from the body of an individual. During hemolysis, the composition of the blood plasma is altered because of the contents of the blood cells spilling into the blood plasma. If the composition of the blood plasma is altered beyond a certain threshold, the blood sample is flagged for hemolysis. If the composition of the blood plasma is altered beyond a higher threshold, the blood sample may become incapable of further use and therefore has to be rejected. Therefore, the object of the invention is to provide a method and device to determine concentration of analytes, particularly extracellular or free hemoglobin, in a whole blood sample. The object of the invention is achieved by a method and a device for determining the concentration of analytes in whole blood.

SUMMARY

A method of determining a concentration of one or more analytes in a sample is disclosed. In one aspect of the invention, the method includes introducing the sample through a channel. Additionally, the method includes generating a cell-free plasma region in the channel, wherein the cell-free plasma region is generated in the channel based on rouleaux effect. The method further includes illuminating the sample with light having one or more varying wavelengths. Furthermore, the method includes obtaining an image of the illuminated sample at each of the wavelengths. The method also includes analyzing the image to determine the concentration of the one or more analytes.

In another aspect, a device for determining the concentration of one or more analytes in a sample includes a channel configured to carry the sample, wherein a cell-free plasma region in generated in the channel based on rouleaux effect. The device further includes a light source configured to emit light at one or more varying wavelengths, wherein the sample is illuminated with light at varying wavelengths using the light source. Additionally, the device includes an image capturing module configured to capture an image of the illuminated sample.

This summary is provided to introduce a selection of concepts in a simplified form that are further described below in the following description. It is not intended to identify features or essential features of the claimed subject matter. Furthermore, the claimed subject matter is not limited to implementations that solve any or all disadvantages noted in any part of this disclosure.

BRIEF DESCRIPTION OF THE DRAWINGS

The present invention is further described hereinafter with reference to illustrated embodiments shown in the accompanying drawings, in which.

DETAILED DESCRIPTION

Figure 1:
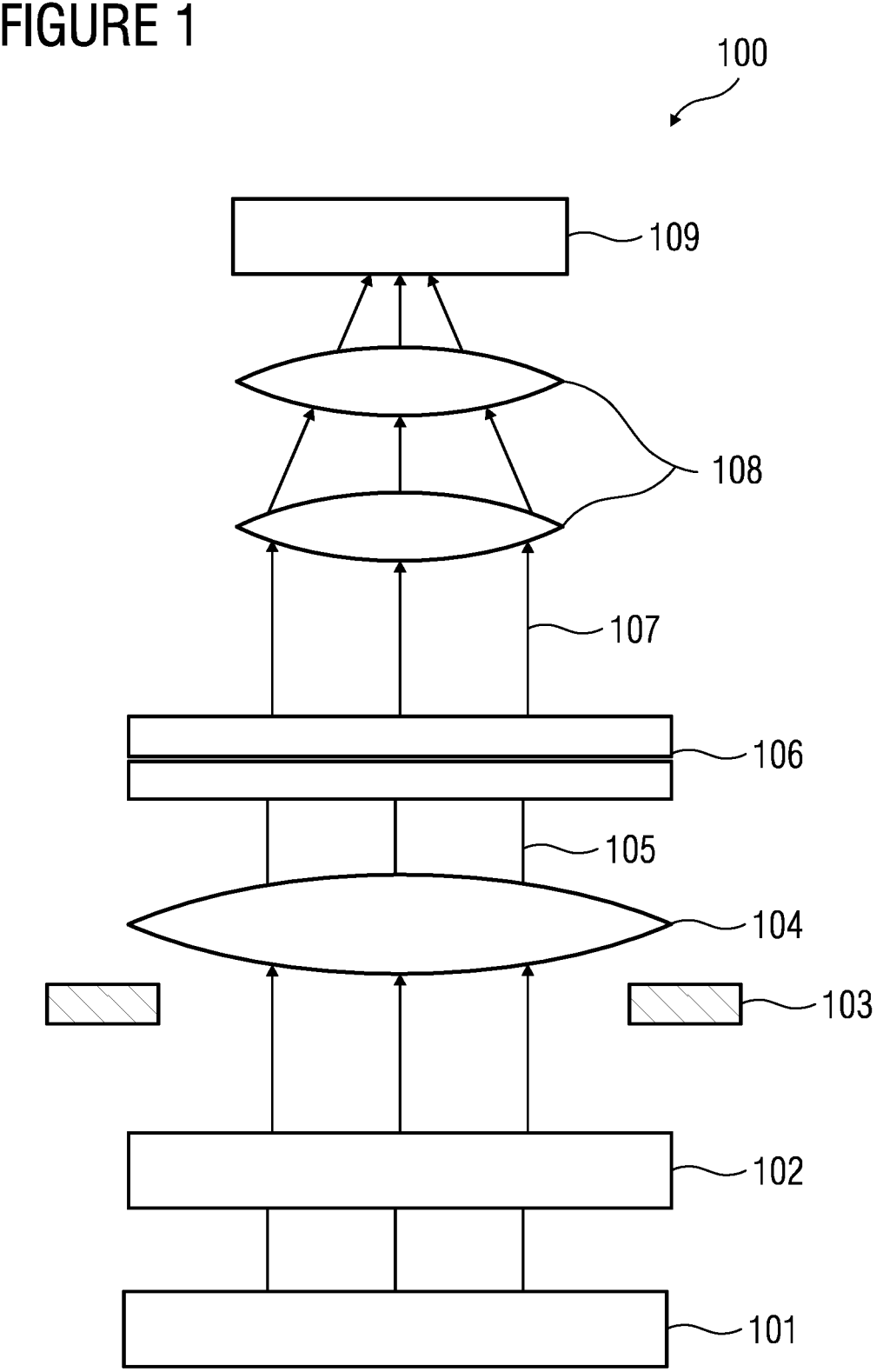
FIG. 1 illustrates an embodiment of a device for determination of a concentration of one or more analytes in the sample.

Hereinafter, embodiments for carrying out the present invention are described in detail. The various embodiments are described with reference to the drawings, wherein like reference numerals are used to refer to like elements throughout. In the following description, for purpose of explanation, numerous specific details are set forth in order to provide a thorough understanding of one or more embodiments. It may be evident that such embodiments may be practiced without these specific details. In other instances, well known materials or methods have not been described in detail in order to avoid unnecessarily obscuring embodiments of the present disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the present disclosure.

Disclosed embodiments provide systems and methods for analyzing a sample. In particular, the method and device may determine a concentration of one or more analytes in a whole blood sample.

FIG. 1 illustrates an illustrative embodiment of a device 100 for determining the concentration of one or more analytes in the whole blood. The device 100 includes a light source 101. The light source 101 may be a multi-wavelength light source, i.e. capable of emitting light at one or more varying wavelengths. In an embodiment, the light source 101 is configured to emit light of at least three different wavelength ranges. The wavelength ranges of the light source 101 may be, for example, between 400 nm and 420 nm; 440 nm and 460 nm; and 520 nm and 650 nm. The wavelength ranges may be defined based on an absorption peak for each analyte to be determined. In an embodiment, the light emitted 105 from the light source 101 may be homogenized using a diffuser 102. The device 100 further includes a channel 106 configured to carry the whole blood sample. The channel 106 may be composed of two planar surfaces of two substantially transparent substrates so as to allow passage of light. The two planar surfaces may be spaced 10 to 30 μm apart. The channel may be, for example, a microfluidic channel. Channel 106 may be a component of a larger device—such as a microfluidic chip. The channel 106 may have a depth in the range between 10 and 30 μm. Therefore, the path length of the light in the channel is low. Described another way, channel 106 can be described as a gap between opposing, parallel surfaces which are substantially planar as well as substantially transparent.

In an embodiment, the microfluidic channel 106 may be created using microspheres between two transparent microscopic slides. Spacer grade microspheres having a diameter in the range of 10 to 30 μm may be used in order to maintain the desired channel 106 (e.g., gap) between microscopic slides. In one illustrative example, the microspheres may be suspended in a liquid medium such that a solution of 10% to 15% microsphere by volume is achieved. The medium may be for example glycerol. The liquid medium enables immobilization of the microspheres. The microspheres may be composed of, for example, but not limited to solid soda lime glass. A small quantity of the microsphere solution in the range of 2 to 5 μL may be placed on two ends of a first microscopic slide. The whole blood sample in the range of 2 to 4 μL may be placed in the center of the first microscopic slide—a sufficient distance from the microsphere solution locations so as to minimize mixing. A second microscopic slide is placed on top of the first microscopic slide. Pressure is applied on the second microscopic slide such that the microspheres in the solution expand. The presence of the microspheres between the two microscopic slides creates a microfluidic channel 106 by maintaining the desired gap. As will be described below, microfluidic channel 106 may then be used in device 100 to obtain a measurement. Suspension of microspheres in glycerol prevents mixing of the whole blood sample with the microspheres.

Figure 4:
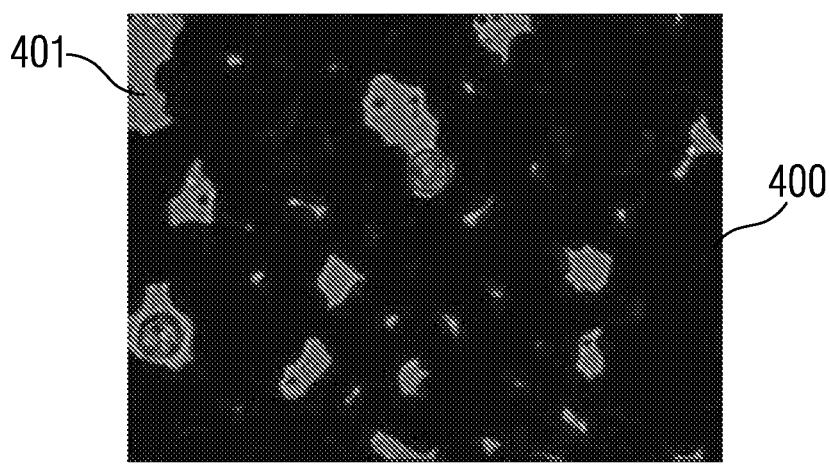
FIG. 4 illustrates an embodiment of an image depicting the phenomenon of rouleaux formation of red blood cells in the channel.

While not wishing to be bound by theory, it is believed that when the channel 106 depth is set to between 10 to 30 μm one or more cell-free plasma regions are generated in the channel 106 due to the rouleaux effect. Under these conditions, the rouleaux effect is utilized to such that red blood cells in a whole blood sample form aggregates. Aggregation of red blood cells may be understood as formation of a linear clump or an aggregated stack of red blood cells. Due to aggregation of the red blood cells, a cell-free plasma region is generated in the channel 106. The aggregation of the red blood cells may also be identified as erythrocyte aggregation. The red blood cells in the whole blood sample may undergo aggregation or rouleaux formation in microfluidic conditions, owing to its unique biconcave shape. Therefore, all the red blood cells aggregate or form rouleaux, thereby generating cell-free plasma region in the microfluidic channel 106, as illustrated in FIG. 4. The light 105 from the light source 101 illuminates the microfluidic channel 106 after passing through an iris 103 and a collimating lens 104. The channel 106 may be transparent so as to allow light from the light source 101 to interact with the whole blood and to be transmitted out 107 of the channel 106. The device 100 additionally includes an imaging capturing module 108, 109. The image capturing module may include imaging lenses 108 and an imaging sensor 109, configured to capture an image of the illuminated microfluidic channel 106. The imaging sensor 108 may be, for example a charge-coupled device (CCD) or a complementary metal oxide semiconductor (CMOS).

Referring to FIG. 4, an image 400 is illustrated which depicts the phenomenon of rouleaux formation of red blood cells in the microfluidic channel 106. The image 400 depicts formation of cell-free plasma regions 401 in the microfluidic channel 106 based on the rouleaux effect on the red blood cells.

Figure 2:
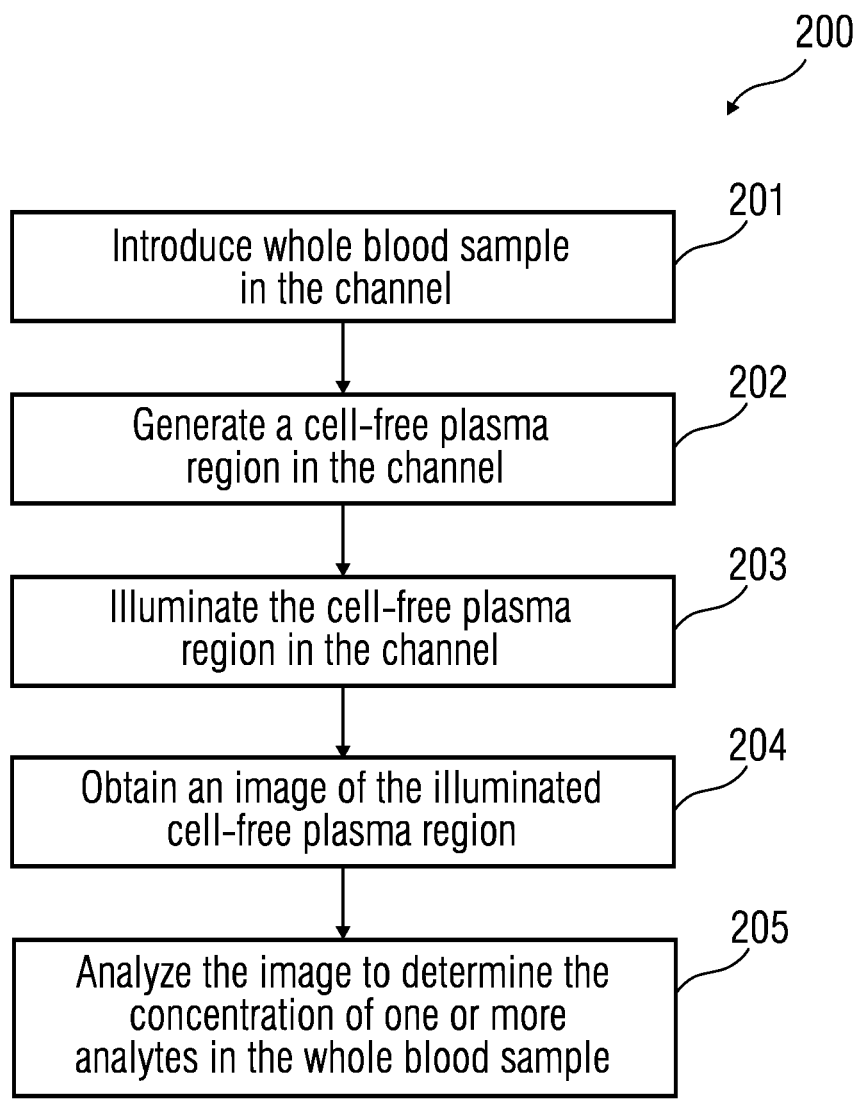
FIG. 2 illustrates a flowchart of an embodiment of a method of determining a concentration of one or more analytes in the sample.

FIG. 2 illustrates a flowchart of an embodiment of a method 200 of determining the concentration of one or more analytes in the whole blood sample. At step 201, the whole blood sample is introduced in the channel 106. The whole blood sample may form a uniform layer in the channel 106. At step 202, a cell-free plasma region 401 is generated in the microfluidic channel 106. The cell-free plasma region 401 may be generated due to rouleaux effect. The path length of the microfluidic channel 106, i.e. the optical path length, is small, i.e. in the range of 10 to 30 μm. Due to this low path length, the red blood cells in the microfluidic channel 106 may form aggregates or rouleaux. Therefore, an active plasma separation method is not needed for separation of plasma from the whole blood. The reduced microfluidic conditions in the channel cause a low path length. Low path length may also result in low absorbance of the light by the analytes in the sample. In spite of the low absorbance, the invention enables determination of the concentration of the analytes in the whole blood. The rouleaux formation may be induced due to physical stress on the red blood cells when the path length is decreased. At step 203, the cell-free plasma region 401 may be illuminated with light having one or more varying wavelengths. The light from the light source 101 may be directed to the microfluidic channel 106 such that the cell-free plasma region 401 is illuminated with the light. The light source 101 may be capable of emitting light at one or more varying wavelengths. Therefore, based on the type of analyte to be determined, the cell-free plasma region 401 may be illuminated with light of one or more varying wavelengths. In an embodiment, the cell-free plasma region may be illuminated with light at wavelengths chosen from a range between 400 nm and 420 nm; 440 nm and 460 nm; and/or 520 nm and 650 nm. The wavelength of the light may be determined based on the absorption peak value associated with the one or more analytes to be determined.

At step 204 of the method 200, an image of the illuminated cell-free plasma region 401 in the channel 106 is obtained. In an embodiment, the image of the cell-free plasma region 401 may be captured using the image capturing module 108, 109. Such image of the cell-free plasma region 401 may be captured each time the plasma region 401 is illuminated with the chosen wavelength(s). Therefore, for example, if the cell-free plasma region 401 is illuminated with light having three different wavelengths, one image for each of the three wavelengths is obtained. At step 205, the captured image is analyzed to determine the concentration of one or more analytes in the whole blood sample. The method steps involved in determining the concentration of one or more analytes is described in detail in FIG. 3.

Figure 3:
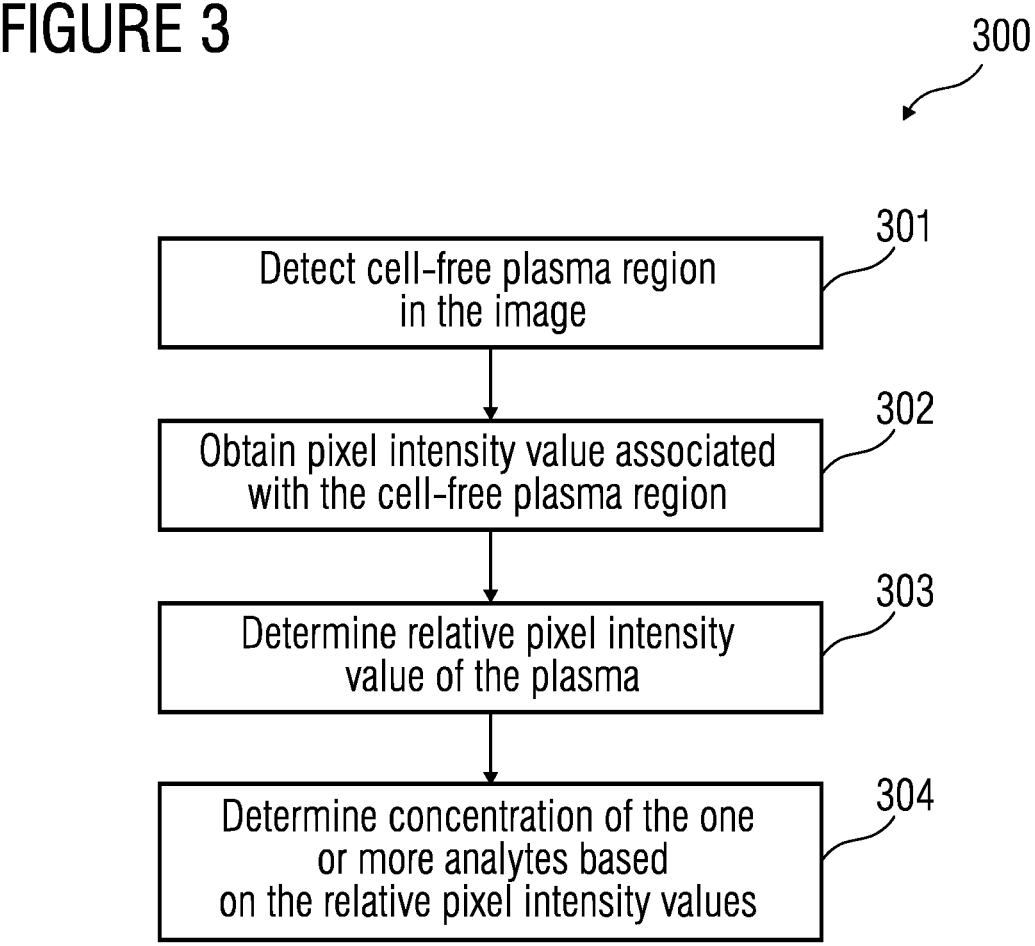
FIG. 3 illustrates a flowchart of an embodiment of a method of analyzing an image to determine the concentration of one or more analytes in the sample.

FIG. 3 illustrates a flowchart of an embodiment of a method 300 of analyzing the image to determine the concentration of one or more analytes in the whole blood sample. At step 301, a cell-free plasma region 401 is detected in the image. The cell-free plasma region 401 may be detected in the image, for example, based on the pixel intensities. A threshold associated with an intensity value of pixels of the cell-free plasma region 401 is determined. The pixels associated with the cell-free plasma region 401 may have a higher intensity pixel value in comparison to pixel value associated with the blood cells (predominantly red blood cells). Therefore, a threshold may be defined such that the cell-free plasma region 401 may be detected in the image based on the threshold.

At step 302 of the method 300, pixel intensity value associated with the cell-free plasma region 401 is obtained. In an experimental embodiment, standard samples of analytes at varying concentrations are prepared. The analyte may be, for example, free hemoglobin. The standard samples are prepared by introducing or spiking free hemoglobin in a normal whole blood sample. Therefore, the standard samples of free hemoglobin may have concentration of free hemoglobin in the range of 100 to 400 mg/dL. The channel 106 containing the standard samples of free hemoglobin may be illuminated with the light source 101 at the wavelength range of 400 nm and 420 nm. Thus, at step 302, the pixel intensity value is obtained for sample containing whole blood only (non-spiked sample); blood sample containing free hemoglobin concentration of 100 mg/dL; blood sample containing free hemoglobin concentration of 200 mg/dL; and blood sample containing free hemoglobin concentration of 400 mg/dL. The pixel intensity values at each of the concentrations may be obtained, for example, at one or more cell-free plasma regions 401 generated in the microfluidic channel 102. For example, for a 16 bit image, the pixel intensity values may range from 0 to 65,535, zero being associated with black and 65,535 being associated with white. Therefore, the pixel intensity values decrease with increasing concentration of free-hemoglobin in the cell-free plasma region. The average pixel intensity value for each of the standard concentrations is obtained.

centration of one or more analytes in the whole blood sample is determined based on the pixel intensity values of the standard samples.

Figure 5:
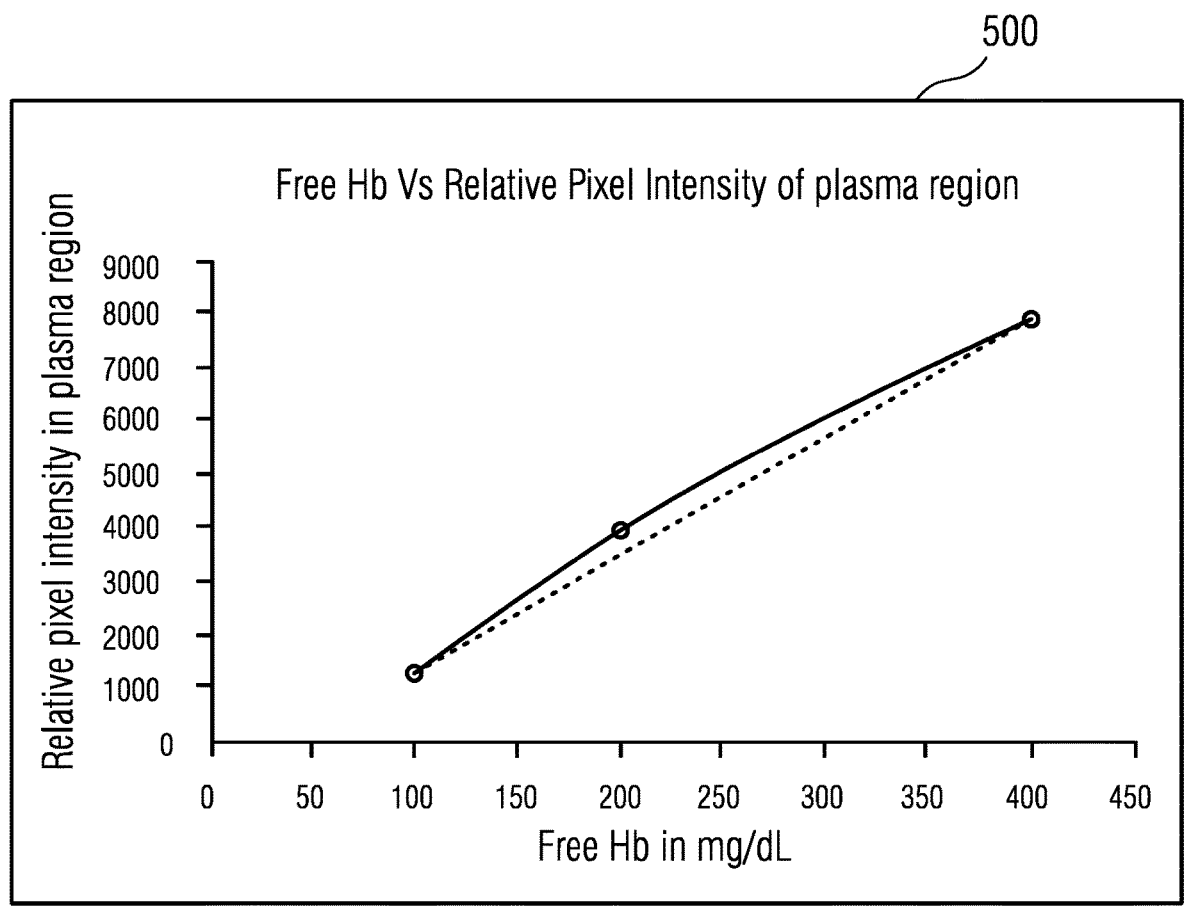
FIG. 5 illustrates an embodiment of a graphical representation of a relation between free-hemoglobin concentration in the cell-free plasma region and relative pixel intensity value of the cell-free plasma region.

FIG. 5 illustrates an embodiment of a graphical representation 500 of a relation between free-hemoglobin concentration in the cell-free plasma region 401 and relative pixel intensity value of the cell-free plasma region 401. As depicted in the graphical representation 500, the relative pixel intensity value of the cell-free plasma region 401 with respect to the non-spiked whole blood sample increases with increasing free-hemoglobin concentration. A linear response is obtained for different free-hemoglobin concentrations.

Advantageously, the concentration of the one or more analytes in the whole blood sample may be achieved without the application of any additional plasma separation technique. The cell-free plasma region 401 is generated in the channel 106 due to formation of rouleaux of red blood cells. The generated cell-free region may be analyzed using standard imaging optics to determine pixel intensity values. Furthermore, no additional reagents or methods are needed to enable plasma separation. Additionally, as the rouleaux formation happens almost instantaneously, the time taken to determine the concentration of the analytes is less.

The foregoing examples have been provided merely for the purpose of explanation and are in no way to be construed as limiting of the present invention disclosed herein. While the invention has been described with reference to various embodiments, it is understood that the words, which have been used herein, are words of description and illustration, rather than words of limitation. Further, although the inven-

| Spiked Hb (mg/dL) | Pixel Intensity Region 1 | Pixel Intensity Region 2 | Pixel Intensity Region 3 | Pixel Intensity Region 4 | Pixel Intensity Region 5 | Pixel Intensity Region 6 | Average | SD | CV | Change in intensity over Only Blood |
|---|---|---|---|---|---|---|---|---|---|---|
| Only Blood | 25406 | 25300 | 25821 | 25106 | 25624 | 25487 | 25457.3 | 249.7 | 0.98 | |
| 100 | 23473 | 24478 | 24536 | 24419 | 24706 | 23529 | 24190.2 | 542.7 | 2.24 | 1267.2 |
| 200 | 21465 | 21284 | 21479 | 21327 | 21983 | 21610 | 21524.7 | 253 | 1.18 | 3932.7 |
| 400 | 17415 | 18143 | 17437 | 17606 | 17573 | 17299 | 17578.8 | 298.1 | 1.7 | 7878.5 |

The above table depicts the pixel intensity values obtained for the non-spiked whole blood sample (Only Blood), and the standard samples of concentrations 100 mg/dL; 200 mg/dL and 400 mg/dL. The pixel intensity values were obtained for six cell-free plasma regions in the microfluidic channel 106. The table also depicts the standard deviation (SD), coefficient of variation (CV) and average pixel intensity values for the samples.

At step 303, the relative pixel intensity of the plasma is determined. In an embodiment, the relative pixel intensity of the plasma may be identified by obtaining a difference between the average pixel intensity value obtained for a specific standard concentration and the average pixel intensity value obtained for the non-spiked whole blood sample. In the above table, the relative pixel intensity for each standard sample is depicted as 'Change in intensity over Only Blood'. The relative pixel intensity of the plasma with respect to non-spiked whole blood sample increases with increasing concentrations of free-hemoglobin in the cell-free plasma region. The relation of concentration of free-hemoglobin with relative pixel intensity value of the cell-free plasma region is depicted in a graphical representation in FIG. 5. The concentration of free-hemoglobin in an unknown sample may be computed based on the pixel intensity values obtained for the known standard concentrations of free-hemoglobin. Therefore, at step 304, the contion has been described herein with reference to particular means, materials, and embodiments, the invention is not intended to be limited to the particulars disclosed herein; rather, the invention extends to all functionally equivalent structures, methods and uses, such as are within the scope of the appended claims. Those skilled in the art, having the benefit of the teachings of this specification, may effect numerous modifications thereto and changes may be made without departing from the scope and spirit of the invention in its aspects.

Below is non-limiting list of illustrative embodiments of the invention:
  (1) An illustrative method of determining a concentration of one or more analytes in a whole blood sample, the method comprising: introducing the sample through a channel; generating a cell-free plasma region in the channel, wherein the cell-free plasma region is generated in the channel based on rouleaux effect, wherein the cell-free plasma region comprises the one or more analytes; illuminating the sample with light having one or more wavelengths; obtaining an image of the illuminated sample at each of the wavelengths; and analyzing the image to determine the concentration of the one or more analytes.
  (2) The illustrative method of (1), wherein the channel is a microfluidic channel, wherein the depth of the channel is in the range of 10-30 micrometer.

(3) The illustrative method according to (1) and (2), wherein analyzing the image comprises: detecting a cell-free plasma region in the image; determining pixel intensity value of the plasma at each of the varying wavelengths; and determining the concentration of the one or more analytes based on the relative pixel intensity value.

(4) The illustrative method according to (3), wherein detecting the cell-free plasma region in the image comprises: defining a threshold of intensity value of pixels associated with the cell-free plasma layer; and detecting the cell-free plasma layer in the image based on the threshold.

(4) The illustrative method according to claims (1) and (2), wherein the cell-free plasma region is illuminated with light having a wavelength in the range between 400 nm to 420 nm; and/or 440 nm to 460 nm; and/or 520 nm to 650 nm.

(5) A device for determining a concentration of one or more analytes in a sample, wherein the device is configured to: receive a channel, wherein the channel is configured to carry the sample, wherein a cell-free plasma region is generated in the channel based on rouleaux effect; and facilitate an interaction of the channel with a light source and an image capturing module.

The illustrative device according to (5), wherein the channel is a microfluidic channel, wherein the channel has a depth in the range of 10-30 micrometer.

The illustrative device according to (5), wherein the light source is configured to emit light at wavelengths in the range between 400 to 420, and/or 440 to 460, and/or 520 to 650.

The illustrative device according (5), wherein the image capturing module comprises one or more lenses and an imaging sensor, wherein the imaging sensor is a charge-coupled device or complementary metal oxide semiconductor.

What is claimed is:

1. A method of determining a concentration of one or more extracellular analytes in a whole blood sample, the method comprising:
    introducing the whole blood sample through a channel, wherein the channel is a microfluidic channel having a depth in a range of from about 10 micrometers to about 30 micrometers;
    generating a first cell-free plasma region in the channel, wherein the first cell-free plasma region is generated in the channel based on rouleaux effect, wherein the first cell-free plasma region comprises the one or more extracellular analytes;
    illuminating the first cell-free plasma region in the channel with light having one or more wavelengths;
    obtaining an image of the illuminated first cell-free plasma region in the channel at each of the one or more wavelengths; and
    analyzing the image to determine the concentration of the one or more extracellular analytes, wherein analyzing the image comprises:
        detecting the first cell-free plasma region in the image;
        determining a pixel intensity value of the first cell-free plasma region at each of the one or more wavelengths; and
        determining the concentration of the one or more extracellular analytes based on a relative pixel intensity value of the first cell-free plasma region with respect to a pixel intensity value of a second cell-free plasma region of a sample with a known concentration of the one or more extracellular analytes.

2. The method according to claim 1, wherein detecting the first cell-free plasma region in the image comprises:
    defining a threshold of intensity value of pixels associated with the first cell-free plasma layer; and
    detecting the first cell-free plasma layer in the image based on the threshold.

3. The method according to claim 1, wherein the cell-free plasma region is illuminated with light having a wavelength in the range between 400 nm to 420 nm.

4. The method according to claim 1, wherein the one or more extracellular analytes comprise free hemoglobin.

5. The method according to claim 1, wherein the cell-free plasma region is illuminated with light having a wavelength in the range between 440 nm to 460 nm.

6. The method according to claim 1, wherein the cell-free plasma region is illuminated with light having a wavelength in the range between 520 nm to 650 nm.

7. A device for determining a concentration of one or more extracellular analytes in a whole blood sample, wherein the device comprises:
    a channel, wherein the channel is a microfluidic channel having a depth in a range of from about 10 micrometers to about 30 micrometers, wherein the channel is configured to carry the whole blood sample, wherein a first cell-free plasma region comprising the one or more extracellular analytes is generated in the channel based on rouleaux effect;
    a light source capable of emitting light at one or more wavelengths and illuminating the microfluidic channel;
    an image capturing module configured to capture an image of the illuminated microfluidic channel; and
    wherein the device facilitates an interaction of the channel with the light source and the image capturing module to determine the concentration of the one or more extracellular analytes based on a relative pixel intensity value of the first cell-free plasma region with respect to a pixel intensity value of a second cell-free plasma region of a sample with a known concentration of the one or more extracellular analytes.

8. The device according to claim 7, wherein the light source is configured to emit light at wavelengths in the range between 400 nm to 420 nm.

9. The device according to claim 7, wherein the image capturing module comprises one or more lenses and an imaging sensor, wherein the imaging sensor is a charge-coupled device or complementary metal oxide semiconductor.

10. The device according to claim 7, wherein the one or more extracellular analytes comprise free hemoglobin.

11. The device according to claim 7, wherein the light source is configured to emit light at wavelengths in the range between 440 nm to 460 nm.

12. The device according to claim 7, wherein the light source is configured to emit light at wavelengths in the range between 520 nm to 650 nm.

13. The device according to claim 7, wherein the channel is transparent.

14. The device according to claim 7, further comprising an iris and collimating lens through which light from the light source passes to illuminate the microfluidic channel.

* * * * *